United States Patent
Wen (10) Patent No.: US 11,241,207 B2
(45) Date of Patent: Feb. 8, 2022

(54) HYBRID CT SYSTEM WITH ADDITIONAL DETECTORS IN CLOSE PROXIMITY TO THE BODY

(71) Applicant: The USA, as represented by the Secretary, Department of Health and Human Services, Bethesda, MD (US)

(72) Inventor: Han Wen, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 66 days.

(21) Appl. No.: 16/639,469

(22) PCT Filed: Aug. 14, 2018

(86) PCT No.: PCT/US2018/046666
§ 371 (c)(1),
(2) Date: Feb. 14, 2020

(87) PCT Pub. No.: WO2019/036446
PCT Pub. Date: Feb. 21, 2019

(65) Prior Publication Data
US 2021/0077045 A1    Mar. 18, 2021

Related U.S. Application Data

(60) Provisional application No. 62/546,639, filed on Aug. 17, 2017.

(51) Int. Cl.
*A61B 6/00* (2006.01)
*G06T 7/10* (2017.01)
(Continued)

(52) U.S. Cl.
CPC .............. *A61B 6/482* (2013.01); *A61B 6/032* (2013.01); *A61B 6/4208* (2013.01);
(Continued)

(58) Field of Classification Search
CPC .......... A61B 6/032; A61B 6/482; A61B 6/00; A61B 6/03; A61B 6/4014; A61B 6/5258; A61B 6/547; A61B 6/585; A61B 6/025; A61B 6/4007; A61B 6/4233; A61B 6/4085; A61B 6/4208; A61B 6/466;
(Continued)

(56) References Cited

U.S. PATENT DOCUMENTS

| 2006/0104415 A1* | 5/2006 | Unger ...................... A61B 6/06 378/62 |
| 2013/0077847 A1* | 3/2013 | Hansis ................... G06T 11/008 382/131 |

(Continued)

*Primary Examiner* — Irakli Kiknadze
(74) *Attorney, Agent, or Firm* — Burns & Levinson LLP; Joseph P. Quinn (57) ABSTRACT

This disclosure generally relates to systems, methods, and devices for performing high-resolution computer tomography (CT) scans providing highly detailed images of particular regions using whole body clinical CT scanners while maintaining high imaging speeds and low dose levels. In particular, the disclosed systems use flat panel detectors in conjunction with common CT detectors to quickly produce high-resolution CT images.

9 Claims, 10 Drawing Sheets

(51) Int. Cl.
*A61B 6/03* (2006.01)
*G06T 11/00* (2006.01)

(52) U.S. Cl.
CPC ............ *A61B 6/5258* (2013.01); *A61B 6/547* (2013.01); *A61B 6/585* (2013.01); *G06T 7/10* (2017.01); *G06T 11/005* (2013.01); *G06T 2207/10081* (2013.01)

(58) Field of Classification Search
CPC ............... A61B 6/5205; A61B 6/5207; A61B 2090/3966; A61B 5/0066; A61B 6/06; A61B 6/145; A61B 6/4452; A61B 6/584; A61B 6/4206; A61B 6/4405; A61B 6/035; A61B 6/4417; A61B 6/037; A61B 6/4258; A61B 6/502; A61B 6/0492; A61B 6/4283; A61B 6/4435; A61B 6/54; A61B 6/587; A61B 6/4423; A61B 6/04; A61B 6/0487; A61B 6/4441; A61B 6/4476; A61B 6/461; A61B 6/465; A61B 6/467; A61B 6/469; A61B 6/548; A61B 6/107; A61B 6/5235; A61B 6/0435; A61B 6/12; A61B 6/4028; A61B 6/405; A61B 8/0825; A61B 8/4416; A61B 6/4266; A61B 5/055; A61B 6/027; A61B 6/4241; A61B 6/5247; A61B 2560/0437; A61B 2560/0443; A61B 2562/166; A61B 2562/227; A61B 6/08; A61B 6/488; A61B 6/4035; G06T 11/005; G06T 5/50; G06T 11/008; G06T 2207/10104; G06T 2207/10072; G06T 2207/10084; G06T 2207/20008; G06T 2207/20221; G06T 2211/416; G06T 7/97; G06T 2207/10088; G06T 2207/10081; G06T 7/10; G06T 11/006; G06T 2210/41; G06T 7/0012; G06T 2207/10116; G06T 2211/424; G06T 2211/432; G06T 5/002; G06T 11/00; G06T 11/203; G06T 2211/421; G06T 11/003; G06T 2207/10032; G06T 2207/20182; G06T 2207/20192; G06T 2207/30004; G06T 2207/10108; G06T 2207/20224; G06T 2207/30024; G06T 1/2985; A61N 2005/1061; A61N 2005/1087; A61N 5/1049; A61N 5/1069; A61N 2005/1052; A61N 5/1065; A61N 5/1064; G01N 23/2076; G01N 23/223; G01N 23/046; G01N 2223/419; G01N 2223/505; G01N 2223/108; G01N 23/2255; G01N 23/04; G01N 21/6428; G01N 2223/401; G01N 2223/501; G01N 2333/025; G01N 23/083; G01N 23/10; G01N 23/20008; G01N 33/54373; G01N 33/54386; G01N 33/58; G01N 33/582; G01N 2223/301; G01N 2223/303; G01N 2223/3037; G01N 2223/3303; G01N 2223/612; A61L 31/026; A61L 31/18; H04N 5/32; H04N 5/347; H01G 11/78; H01G 9/048; H01G 9/145; H01L 27/14618; G02B 6/4239; G02B 1/04
USPC .............................................. 378/4, 9, 19, 62
See application file for complete search history.

(56) References Cited

U.S. PATENT DOCUMENTS

| | | | | |
|---|---|---|---|---|
| 2014/0016849 A1* | 1/2014 | Brown | ...................... | G06T 5/50 382/131 |
| 2014/0037047 A1* | 2/2014 | Tsukagoshi | .......... | A61B 6/4266 378/16 |
| 2014/0314199 A1* | 10/2014 | Shi | ...................... | A61B 6/4233 378/9 |
| 2016/0071245 A1* | 3/2016 | Bergner | ................ | G06T 11/003 382/131 |
| 2016/0345928 A1* | 12/2016 | Jung | .................... | A61B 6/4464 |
| 2018/0132799 A1* | 5/2018 | Nakanishi | ............... | A61B 6/545 |
| 2019/0120977 A1* | 4/2019 | Jacobs | ................. | G01T 1/2018 |

\* cited by examiner

PRIOR ART

FIG. 3A

PRIOR ART

HYBRID CT SYSTEM WITH ADDITIONAL DETECTORS IN CLOSE PROXIMITY TO THE BODY

CROSS REFERENCE TO RELATED APPLICATIONS

This application claims priority to U.S. Provisional Application No. 62/546,639, filed Aug. 17, 2017 which is hereby incorporated herein by reference in its entirety.

GOVERNMENT INTEREST STATEMENT

This application is a US national phase application of PCT application No. PCT/US18/46666 filed on Aug. 14, 2018, which claims priority to U.S. Provisional Application No. 62/546,639, filed Aug. 17, 2017, which are hereby incorporated herein by reference in their entirety.

FIELD

The present disclosure relates to systems, methods, and devices for performing high-resolution computer tomography (CT) scans providing highly detailed images of particular regions using whole body clinical CT scanners while maintaining high imaging speeds and low dose levels.

BACKGROUND

CT imaging is used in the diagnosis and study of many diseases and conditions. CT tissue texture information is important for monitoring cystic fibrosis or lung cancer in defining exacerbations and stages of disease. For example, improved visualization of lung parenchyma and the margins of lung cysts may provide sufficient detail to distinguish the types of cystic lesions (such as a non-invasive "virtual biopsy") such that the typical lung tissue pathologic biopsy is not needed to make a diagnosis. Current diagnosis of lung disease increasingly uses CT as the imaging method: annual low-dose CT exams are the recommended screening for lung cancer in asymptomatic smokers between ages 55 and 80. In another example, CT texture information of the margins of lung nodules is also an important marker in lung cancer detection and staging.

SUMMARY

The present disclosure generally relates to systems and methods for performing high-resolution x-ray computed tomography (CT) that enables a high-resolution "zoom-in" scan in a clinical CT system by placing additional x-ray detector panels near the patient's body. In one aspect, the detector panels are positioned out of view during a standard CT scan and then moved in position for a secondary high-resolution scan. In another aspect, the data from the full rotation CT scan, gathered while the detector panels are in position, is used to improve the reconstruction of the high-resolution scan and to provide information on the location of the panel detectors in situ, which is also used in image reconstruction.

According to one embodiment, a method for performing hybrid CT imaging using a whole body CT scanner includes the steps of performing a low-dose CT scan and determining if a high-resolution scan is desired. If a high-resolution scan is desired, the method further includes positioning a flat panel detector near a region of interest and performing a high-resolution scan of the region of interest. Lastly, a high-resolution image is reconstructed from the high-resolution scan.

In another embodiment, a method for performing hybrid CT imaging using a whole body CT scanner includes performing a full rotation CT scan and positioning one or more panel detectors in proximal to a patient in the whole body scanner. A hybrid CT scan is performed, where the one or more panel detectors and a CT detector of the whole body CT scanner acquire data in parallel. Another hybrid CT scan is performed, where an x-ray source fires over the full rotation but with a time-varying intensity profile, and the x-ray source intensity is greater over an arc opposite the one or more panel detectors, and lower in the rest of the rotation. Lastly, a low-resolution and a high-resolution image are reconstructed from the acquired data.

The various methods of CT imaging performed herein may be performed on an embodiment of a hybrid CT system for performing low-resolution CT imaging and high-resolution CT imaging that includes a CT scanner system further comprising an X-ray source, a CT detector, and a processing system for image reconstruction. The system also includes at least one mobile panel detector.

Additional objectives, advantages, and novel features will be set forth in the description that follows or will become apparent to those skilled in the art upon examination of the drawings and detailed description that follows.

Reference characters indicate corresponding elements among the views of the drawings. The headings used in the figures do not limit the scope of the claims.

DETAILED DESCRIPTION

The present disclosure relates to an improved system and method for performing CT imaging that uses a whole body CT scanner in conjunction with one or more "mobile/flat" panel detectors in close proximity to the patient's body. The combined scanner and panel configuration is a hybrid scanning system that provides high resolution while maintaining speed, low dose and convenience of workflow. A "zoom-in" capability for a detailed "closer look" at particular regions is useful in a variety of applications including, but not limited to: lumbar spine CT/myelogram, renal and pelvic CT, CT colonoscopy, pediatric CT, and CT angiography. High-resolution CT is used in Digital breast tomosynthesis (DBT), commonly referred to as three-dimensional (3-D) mammography, and other dedicated CT platforms, although at slower speeds than required for whole body scale CT.

Figure 1:
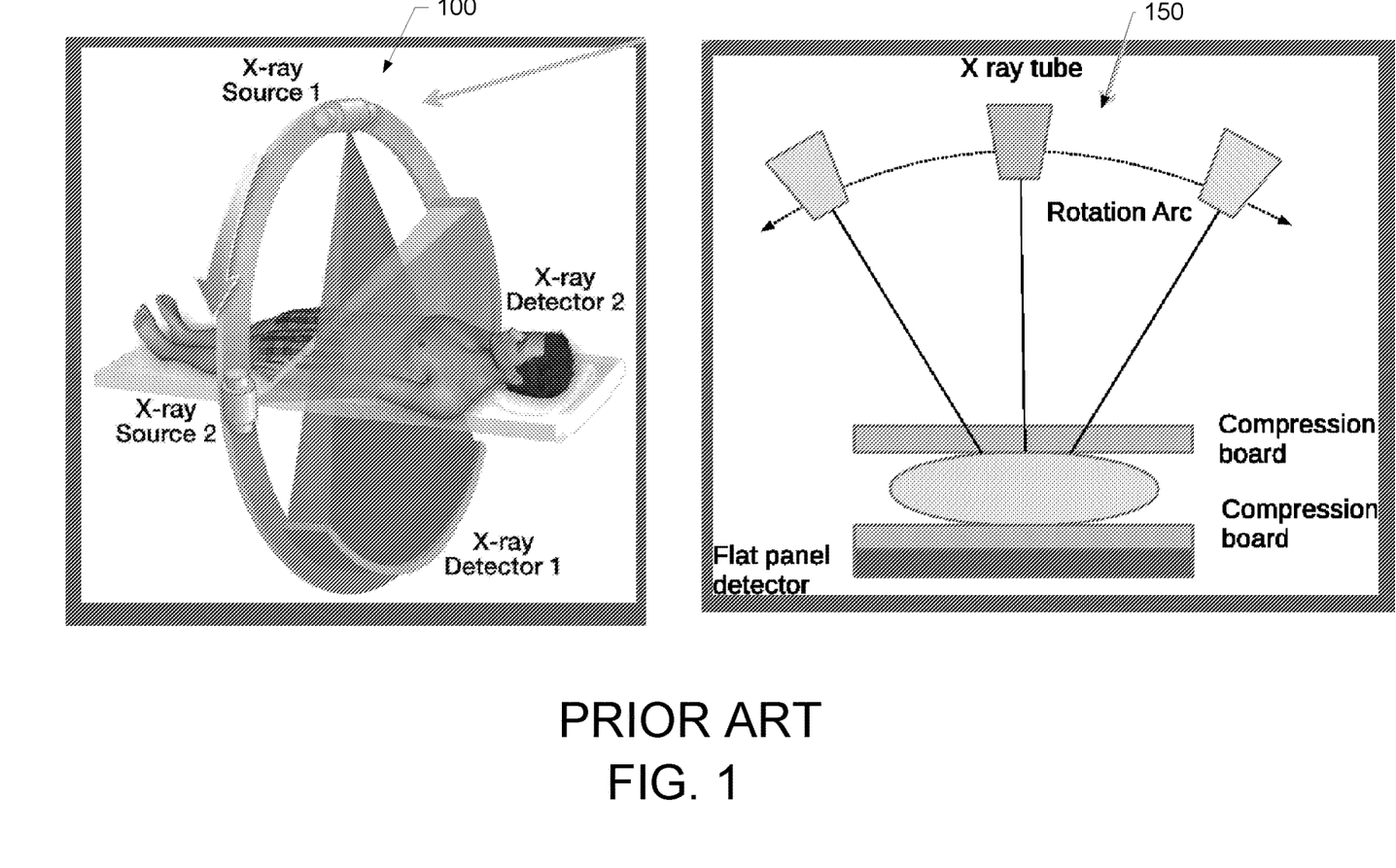
FIG. 1 are illustrations of a typical CT system and a 3-D mammography system.

Typically, there are three main factors that influence the resolution and speed of a CT system: x-ray source power and spot size, detector resolution, and detector proximity to the body. Current whole body CT systems have high power x-ray sources to ensure speed, but not the proximity of the detector for high resolution. Whole body CT uses a powerful x-ray tube and high gantry speed; however, it provides low resolution images. Conversely, 3-D mammography produces high-resolution images yet typically uses lower-powered x-ray tubes and slower gantry speeds. FIG. 1 includes illustrations of typical detector and x-ray source configurations for typical CT scanners 100 and 3-D mammography systems 150.

Figure 2:
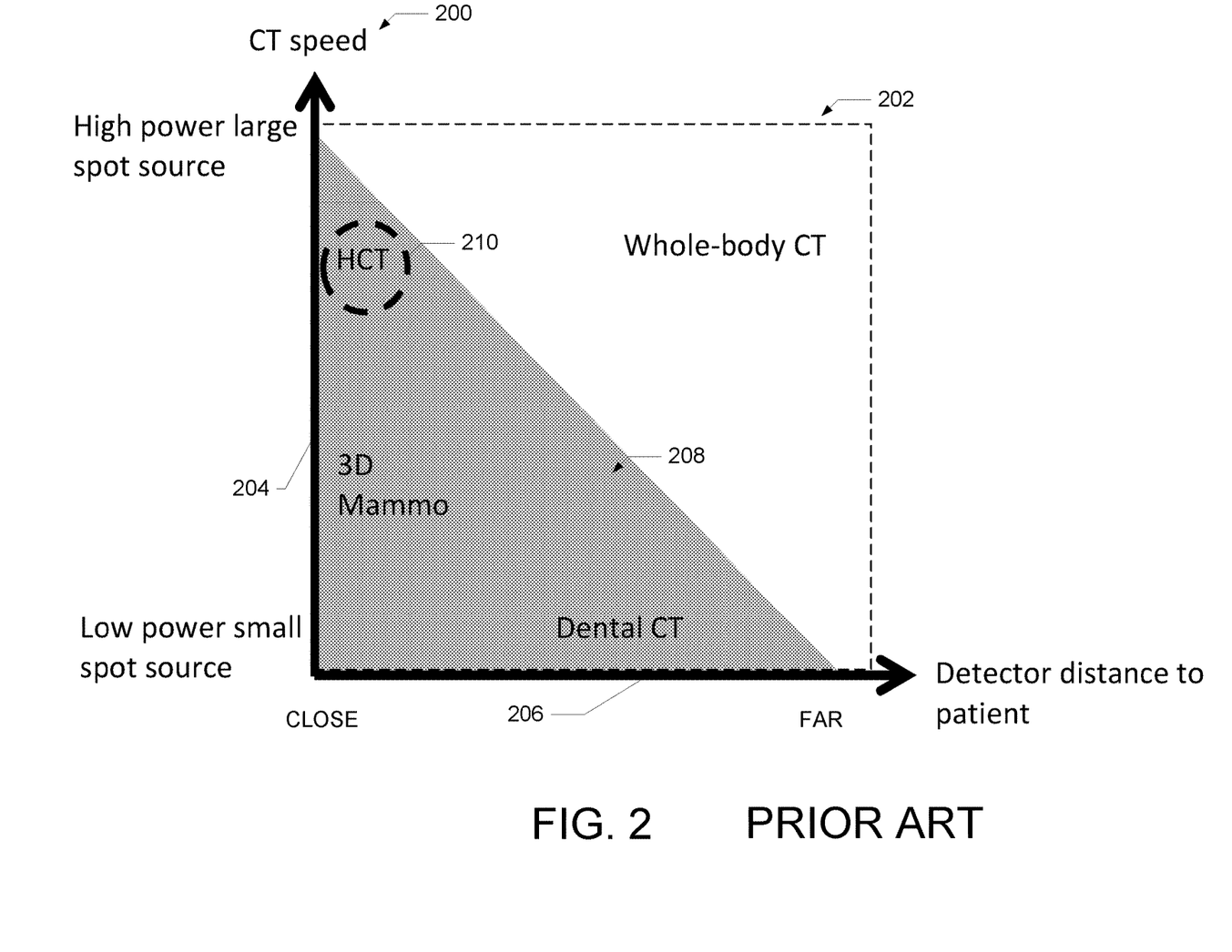
FIG. 2 is a graph illustrating various factors that affect CT imaging resolution and performance.

FIG. 2 is a graph illustrating typical determinants of imaging speed and resolution assuming that detector resolution and performance is not a limiting factor. As shown, overall imaging speed 200 and resolution 202 typically depend on x-ray source power and the size or area of the spot in the x-ray source that emits the x-ray beam, both indicated as 204, as well as the detector-to-patient distance, indicated as 206. The typical operating parameters for common x-ray imaging procedures, such as 3-D mammography and dental CT scans, are also shown for reference. The high-resolution area is generally indicated as 208, while the operating area provided by the hybrid CT (HCT) system of the present disclosure lies in the circular HCT region 210.

Figure 3A:
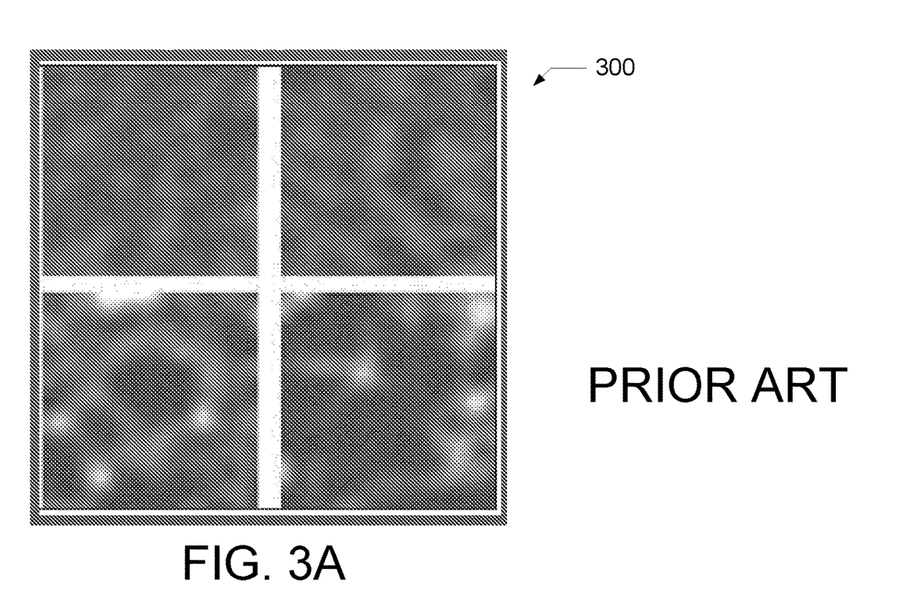
FIG. 3A is a standard image taken from a standard CT system.
Figure 3B:
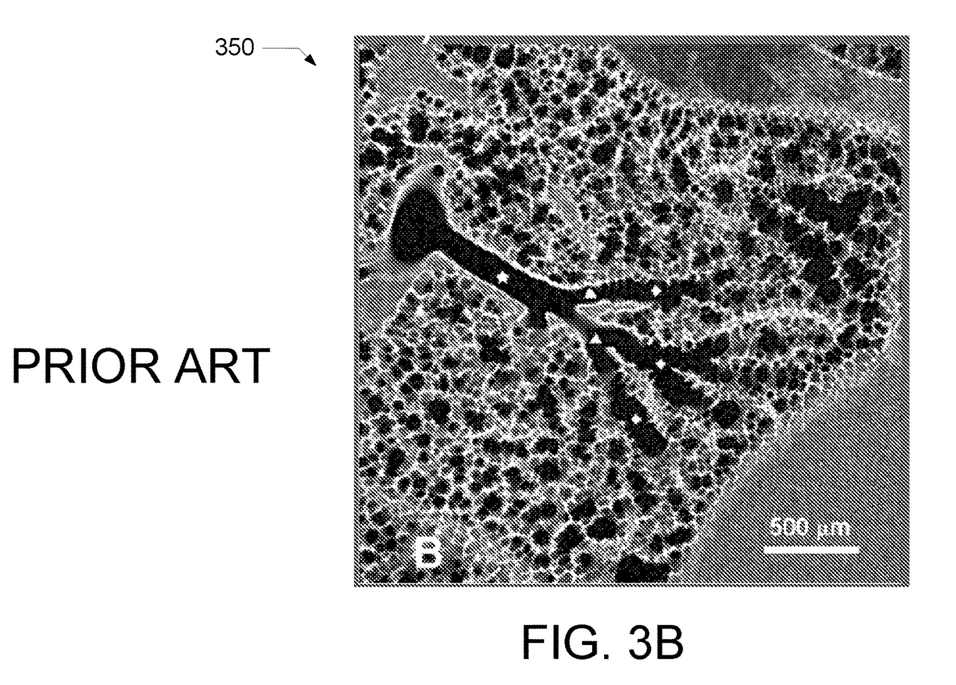
FIG. 3B is a standard image taken from an X-ray microtomography imaging system.

Various studies have shown that ultra-low dose CT is capable of distinguishing and quantifying the cystic lung lesions characteristic of lymphangioleiomyomatosis (LAM). Furthermore, when using normal-dose CT, the areas surrounding the cysts can be quantified based on their texture, which correlates with various measures of pulmonary function. Therefore, the hybrid CT system can be applied to common lung diseases such as COPD, as well as rare lung diseases such as LAM and cystic fibrosis. In one aspect, CT images of tissue texture provide important biomarkers for the detection and staging of COPD, cystic lung disease, and lung cancer. By way of example, FIGS. 3A and 3B include images from a standard Clinical CT 300 and a Synchrotron microCT image 350, respectively. One desired use of the systems and methods disclosed herein is to provide high-resolution imaging, similar to the microCT image, for a variety of organs and structures to provide greater data and potentially limit the necessity for biopsy procedures, while maintaining the speed and safety of standard CT scans.

The hybrid CT systems and methods disclosed herein use one or more movable flat panel detectors (FPDs) that are positioned within a whole body CT scanner to provide high-resolution images of desired portions of the patient. FPDs may also include curved-surface panel detectors that conform to the contour of the patient's body. The high-resolution images are typically taken after an initial CT scan is performed using the whole body detectors that are normally used with the CT system. After this initial scan, one or more mobile flat panel detectors are positioned in close proximity to the patient's body, such as in the patient bed or on top of the patient, in a clinical whole body CT scanner to form a hybrid system. For example, the FPDs are movable in the X and Z directions under or over the patient. They can be positioned out of the CT view under the targeted region. Once the FPDs have been positioned, a limited-angle tomography scan with the CT x-ray tube may be performed.

The use of the FPDs reduces the detector-to-body distance, which improves resolution by reducing the penumbra of the x-ray source spot in the capture images. In various embodiments, this distance may be reduced by as much as two-thirds, or approximately 70%. In other testing described herein, the images gathered using the FPDs provided approximately three times the resolution of the CT scanner in radiography mode.

As used herein, a detector generally refers to the devices, systems, or apparatuses that detect x-rays and the absence of x-rays after an x-ray beam is projected through an object. The present system may be used with both digital or photographic x-ray plates and films. Image reconstruction may be performed on any suitable computer or processing system. A common CT system 100 and the hybrid CT system 400 may be in communication with one or more processing systems, having a processor and memory, for storing data, performing image reconstruction at one or more processors, for configuring imaging protocols performed with the scanning systems, and for the operation of the imaging systems.

Figure 4A:
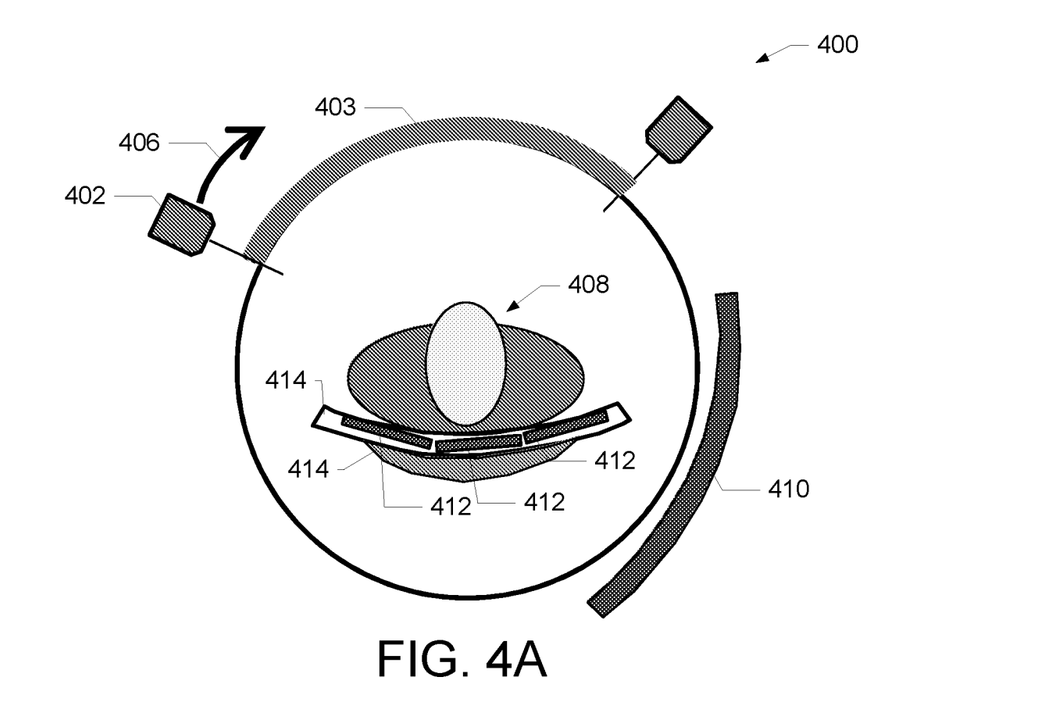
FIG. 4A is an illustration of the hybrid CT system wherein the x-ray sources fire continuously during a scan according to one embodiment.
Figure 4B:
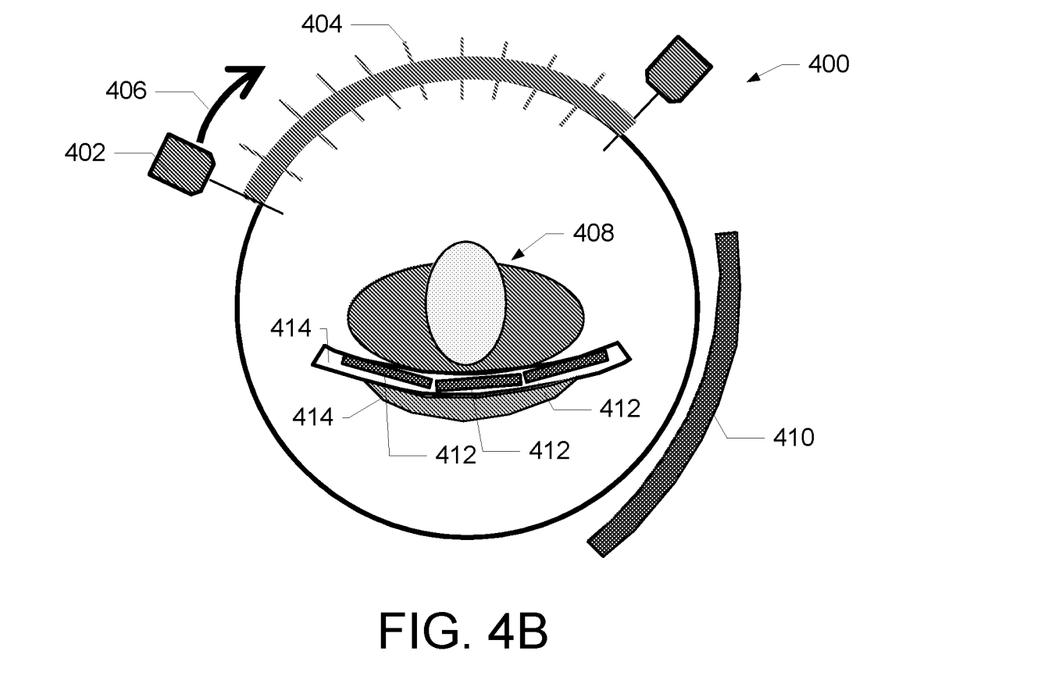
FIG. 4B is an illustration of the hybrid CT system wherein the x-ray sources fire intermittently during a scan according to one embodiment.

FIGS. 4A and 4B illustrate an embodiment of the hybrid CT system 400. During imaging, the x-ray source 402 fires continuously, indicated as 403 in FIG. 4A, or the x-ray source fires in pulses, indicated as 404 in FIG. 4B, while traversing along an arc 406, above the patient 408. The CT detector 410 acquires images during the scan for geometric calibration purposes. One or more flat panel detectors 412 acquire images at high frame rates. In various embodiments, one or more FPDs may be stationary. Alternatively, one or more FPDs may be mobile or positioned within or proximal to the bed portion 414 of the CT scanner. In embodiments where the FPDs are mobile, their movements about the CT bed or patient may be synchronized to move in tandem with the x-ray source 402. In one embodiment, an FPD 412 is placed in a frame 416 positioned behind the patient's back. The FPD 412 is moved into the optimal position to cover a region of interest in the patient's chest for the secondary high-resolution scan. The x-ray source 402 fires in a limited arc, similar to the arc 406, that is optimized for imaging a desired region of interest (ROI). During this limited arc scan, the x-ray source 402 may operate continuously, or in pulses according to a desired imaging protocol. In various embodiments, the x-ray source 402 is operated using the same protocol as during the initial CT scan. Alternatively, the x-ray source 402 may operate using a different protocol than the protocol of the initial CT scan. According to other embodiments, the FPD 412 can also move in tandem with the x-ray source 402 to best cover the ROI, or it may be stationary during the scan. During the limited arc scan, the CT detector simultaneously acquires data to determine location of the FPD 412 in situ.

When operated either continuously as shown in FIG. 4A, or in a pulsed manner as shown in FIG. 4B, the CT detector 410 acquires images of the patient 408 and the FPDs 412 during the scan for geometric calibration purposes. In an embodiment, the FPDs 412 may acquire images at approximately 100-10000 frames per second (fps). In various embodiments, the FPDs may acquire images at at least 100 fps, at least 500 fps, at least 1000 fps, at least 2000 fps, at least 5000 fps, or at least 10000 fps. In one embodiment, the FPDs 412 acquire images in sync with the x-ray pulses in a range of approximately 200-1000 fps. In one embodiment, the FPDs acquire images at at least 400 fps. In various embodiments, the secondary high-resolution scan may be performed in at least 0.1 seconds, at least 0.3 seconds, at least 1 second, at least 3 seconds, at least 10 seconds, at least 20 seconds, or at least 30 seconds. In one embodiment, the secondary high-resolution scan may be performed in 1 second or less. In an embodiment, the secondary high-resolution scan is performed in 0.3 seconds.

The x-ray dose to which the patient is exposed during the high-resolution scanning is similar to that of a normal CT dose; however, it is focused to a smaller region of interest. As such, the overall dosage may be less than a low-dose CT due to the small window of the scan and the small corresponding area of the patient examined. For the important dose consideration, the radiation density in the region of interest can be multiple times the level of a low-dose CT and still within the operating range of a clinical CT scanner, while the size of the exposure window is limited to the region of interest, for example, around a lung nodule, a vertebra of the spine, or a tumor in the colon, such that the effective dose will be at or below a low-dose CT. The dose addition on top of the screening scan can be justified with potential benefits such as avoiding biopsy. Furthermore, the hybrid CT system is also well-suited for use with patients where dosage is not an issue. For example, where targeted scanning is necessary or where patients are well within annual x-ray exposure limits, the hybrid CT system may perform multiple scans in short periods to provide highly accurate imaging data. In various aspects, the CT dose index (CTDIvol) of the hybrid CT system may be at least 0.01 mGy, at least 0.1 mGy, at least 1.0 mGy, at least 10 mGy, or at least 100 mGy. In one embodiment, the CTDIvol of the CT hybrid system may be approximately 0.1 mGy.

Example Methods of Performing Hybrid CT Scans

Figure 5A:
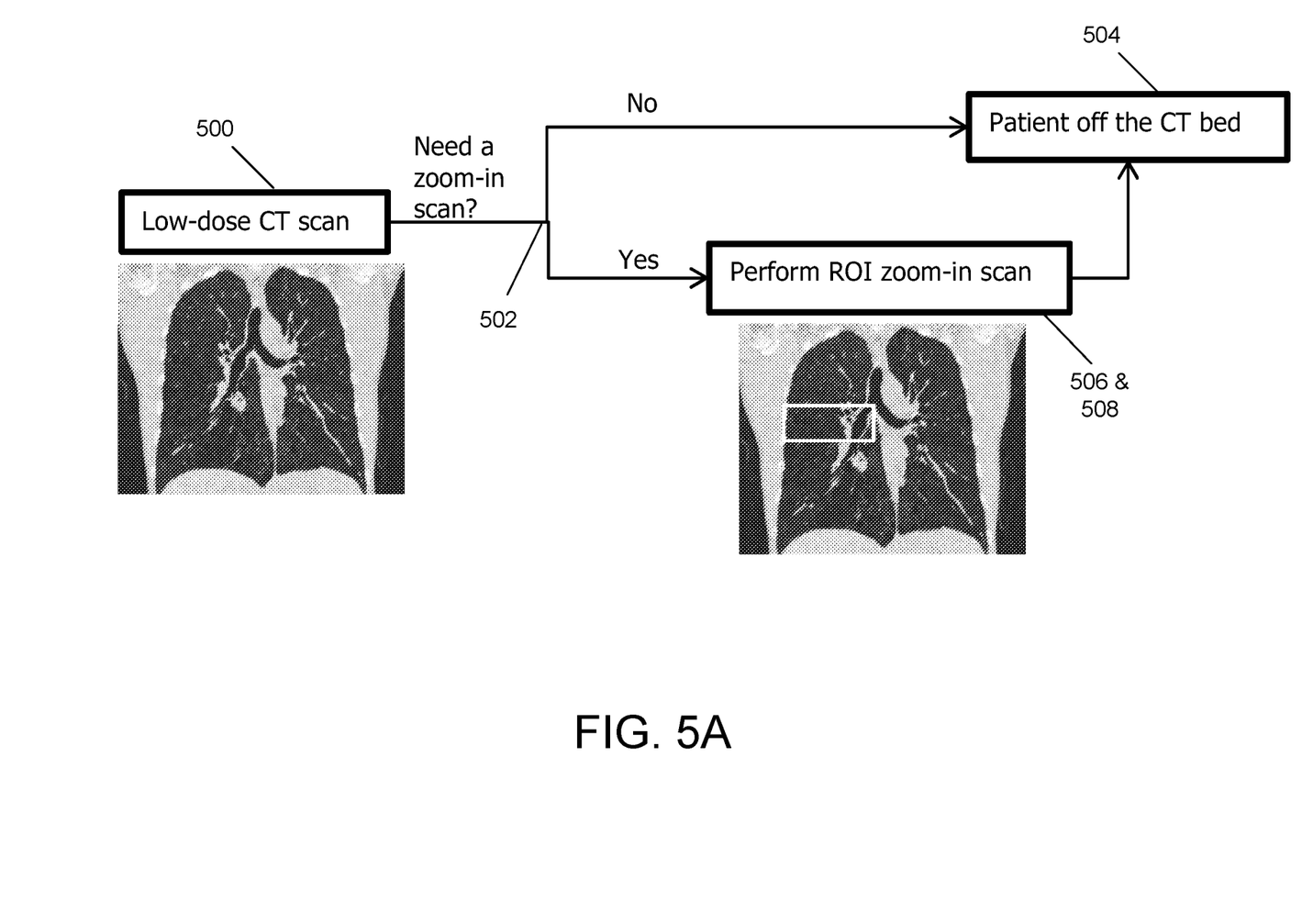
FIG. 5A is a flowchart of a method for performing a standard resolution scan and a high-resolution scan using the hybrid CT system according to one embodiment.
Figure 5B:
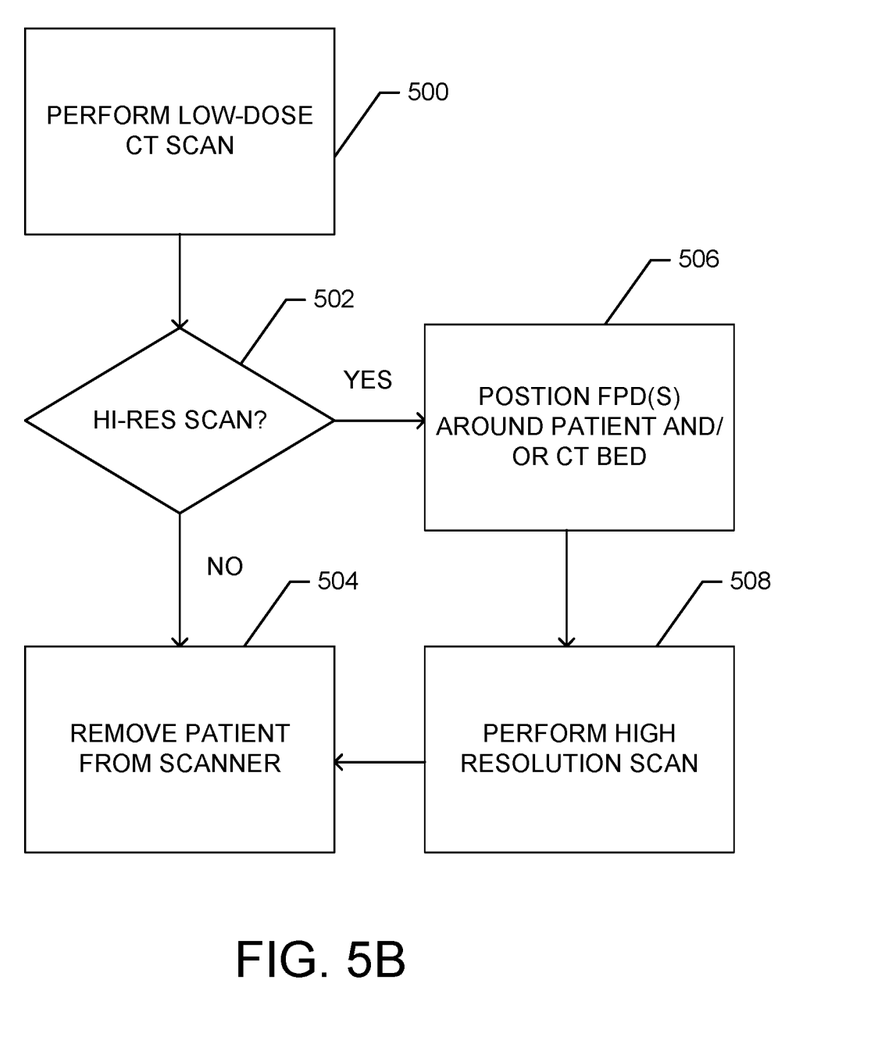
FIG. 5B is a flowchart of another method for performing a standard resolution scan and a high-resolution scan using the hybrid CT system according to one embodiment.

A method of performing a CT scan according to one embodiment of the disclosed method is shown and illustrated in reference to FIGS. 5A-5B. At step 500, a low-dose screening scan is performed. At 502, a determination whether a close-up high-resolution scan is desired is made upon review of the low-dose scan. By way of example, a close-up view of a particular region, such as, but not limited to the area around lung cysts, nodules or a segment of the spine, may be desired. If it is determined that a high-resolution scan is not performed, then the patient may be removed from the CT scanner at step 504. Conversely, if a high-resolution scan of a particular ROI is desired, one or more FPDs are automatically positioned optimally over the region of interest, at 506, and a series of images are acquired at high-resolution and high-frame rate by the FPDs either continuously or in sync with the x-ray pulses at 508. In various aspects, the secondary high-resolution scan may be performed in 10 seconds or less.

During image reconstruction, the data captured from FPDs is processed into a three (3) dimensional volume of the region of interest. According to various embodiments, more than one ROI can be imaged in the same scan by segmenting the x-ray beam of the CT scanner with adjustable masks on the x-ray source and positioning one or more FPDs in line with the ROIs simultaneously.

Figure 6:
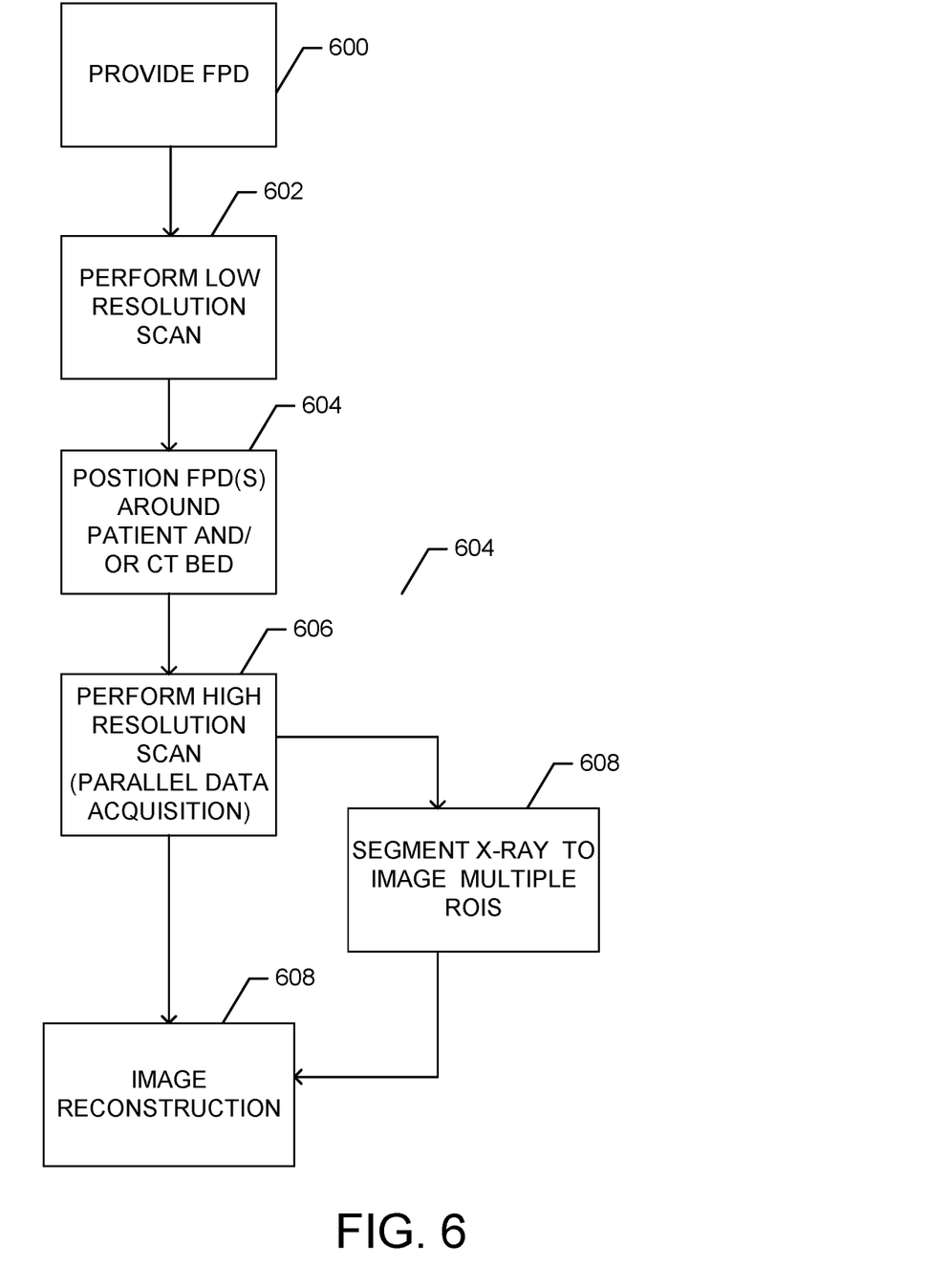
FIG. 6 is a flowchart of another method for performing a standard resolution scan and a high-resolution scan using the hybrid CT system according to one embodiment.

According to another embodiment, a method of performing a hybrid CT scan includes positioning one or more panel detectors in close proximity to the body in a standard CT scanner at 600. However, during an initial scan, the FPDs are positioned out of view or in a position where they will not be visible when acquiring an initial full rotation standard CT scan at 602. Next, at 604 the FPDs are positioned to cover the region of interest, then, at 606, a scan is performed where the FPDs and the CT detector acquire data in parallel during the "zoom-in" scan. The full rotation CT data is used to provide boundary conditions and suppress low-spatial-frequency artifacts in the reconstruction of the high-resolution zoom-in scan at 608. The parallel CT detector data is used to determine the positions and orientations of the FPDs for geometric calibration in situ. In various embodiments, the method may optionally include segmenting the x-ray beam into multiple portions using a collimator or masks to image more than one region of interest at 607.

In another aspect of the systems and methods disclosed herein, the FPDs can be manufactured or configured to be transparent for x-ray photons of energies that are above a pre-determined threshold. As such, the FPDs may preferentially capture lower energy photons and be transparent to higher energy x-ray photons. For embodiments where the FPDs are configured to capture x-rays at selective energy levels, the CT detector will capture more high energy photons that would otherwise be blocked by the FPDs to improve the CT data for alignment purposes, while the FPDs only capture lower energy photons for better image contrast and lower image noise. As previously mentioned, when used to image patients where x-ray dosage is not a primary concern, then simultaneous survey and high-resolution scanning may be performed, where high energy x-rays may be used over large areas including the ROIs aligned with the FPDs.

In a typical clinical CT scanner, the CT scanner detector has a pixel physical size in a range between approximately 300-800 μm, while the detector is, by way of example, approximately 45 cm from the targeted region. Conversely, images captured using the hybrid system with one or more FPDs in place provide a detector pixel physical size of approximately 50-150 μm and an exemplary distance between detector to lung center distance of 15 cm.

The use of the FPDs in the hybrid CT system provides many other useful technical features over existing CT imaging. For example, as the CT detector acquires images simultaneously with the FPDs during the high-resolution scan, the CT scanner data also provides 3-D position data of the FPDs that is used in the reconstruction of the high-resolution scan. In one aspect, the standard CT screening scan helps eliminate artifacts in the subsequent high-resolution scans. In particular, shadows created during the limited-angle high-resolution imaging are removed during reconstruction using the data. Similarly, the data collected from the CT detector during the high-resolution tomography scan also provides surface detector position information in situ, crucial for creating the high-resolution images. The CT volume data provides constraints for the limited-angle tomography reconstruction of the high-resolution scan.

Referring to FIGS. 4A and 4B about the firing arc of the x-ray source, the x-ray source can be firing at a low level when traversing the rest of the circle outside the arc, to allow the CT detector to collect data over the full rotation. Thus, the images of the FPDs and other high contrast objects in the body such as bones and implants, as obtained from the CT detector, are better defined. The additional data provides at least three additional benefits over traditional CT imaging. First, the additional FPD images provide more accurate positions of the FPDs in three-dimensional (3-D) space. This improves reconstruction of the high-resolution scan. Second, better images of high contrast objects in the body from the parallel CT detector during the high-resolution scan improve the 3-D registration between images reconstructed from the FPDs during the high-resolution scan and images reconstructed from the standard scan. This improves the suppression of blurring artifacts in the high-resolution scan using data obtained from the standard scan. Third, improved images of high contrast objects in the body obtained from the parallel CT detector during the high-resolution scan are directly used to suppress blurring artifacts arising from such objects in the high-resolution images from the FPDs. For example, the parallel CT volume data collected from the CT detector during the high-resolution tomography scan also provides 3D images of high contrast objects in the body such as bones and implants. This information can also be used to remove the artifacts in the high-resolution tomography images which originate from these high-contrast objects. Such objects are responsible for the most severe artifacts in the high-resolution tomography.

Studies and Experiments

Figure 7A:
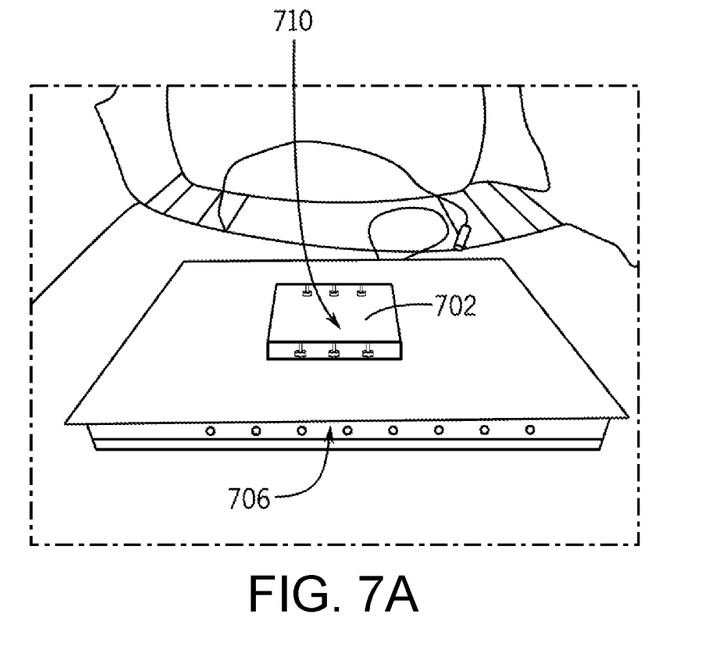
FIG. 7A is a picture of a test target used in one experimental study of an embodiment of the hybrid CT system.
Figure 7B:
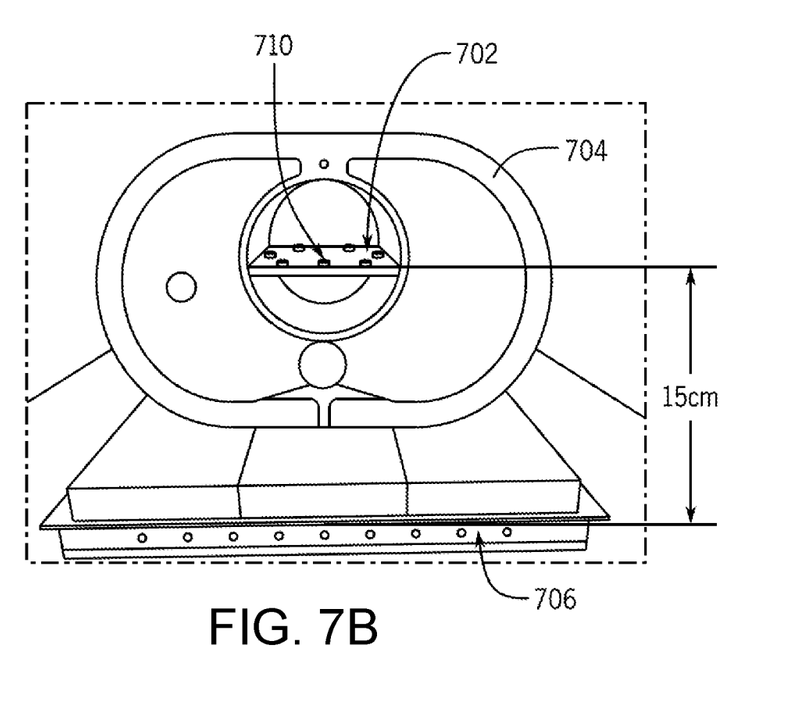
FIG. 7B is a picture of a test target in a chest phantom used in one experimental study of an embodiment of the hybrid CT system.

FIGS. 7A and 7B depict test configurations 700A-B used in an experimental simulation of the CT hybrid system. As shown, a resolution target 702 is placed in the middle of a standard chest phantom 704 in a clinical whole body CT scanner on top of an FPD 706 placed on the CT bed 708. The x-ray source was used to acquire two-dimensional projection images of the phantom. As shown in FIG. 8, the data captured by the FPD provided approximately three times the resolution of the CT scanner detector.

The CT scanner used in simulation was an Aquilion Genesis system by Toshiba. The CT scanner was operated at 120 kV/20 mA, while a Paxscan FPD was used for the high-resolution images. The Paxscan FPD had a pixel size of approximately 83 µm, captured data at approximately 2 fps, and included a 2 mm Aluminum filter. The target 702 included a collection of tungsten wires 710 approximately 50 µm in width.

The test also included a regular CT scan with the target 702 placed in the center of the chest phantom 704 for reference. The reference scan was performed with the following parameters: 135 kV, 220 mA, with a 1 s gantry rotation. The collected reference data was reconstructed into 1 mm slices of approximately 20 mm diameter with a kernel of an FC51 kernel.

Figure 8A:
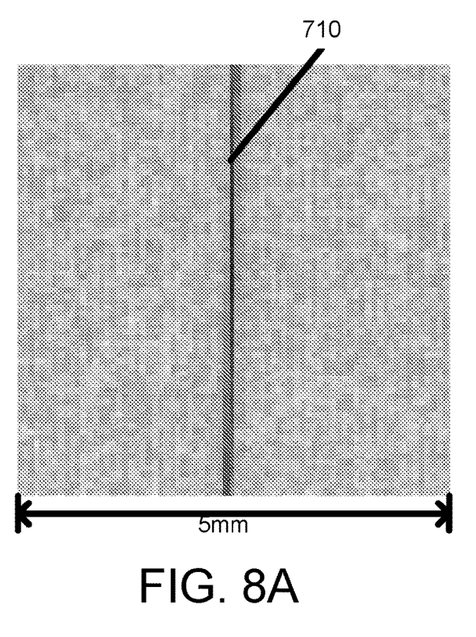
FIG. 8 are example images captured during the experimental study of an embodiment of the hybrid CT system.
Figure 8B:
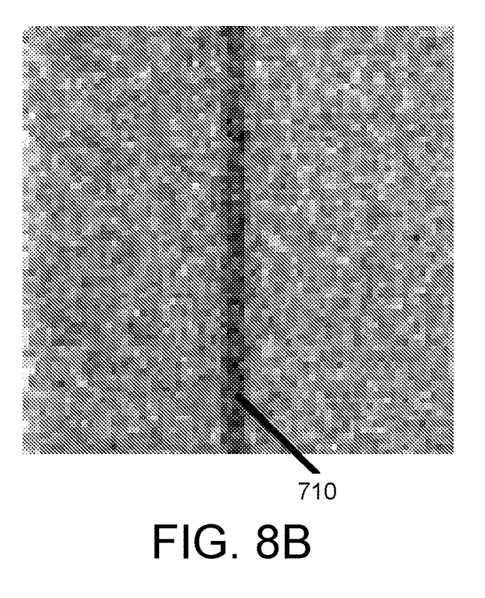
Figure 8C:
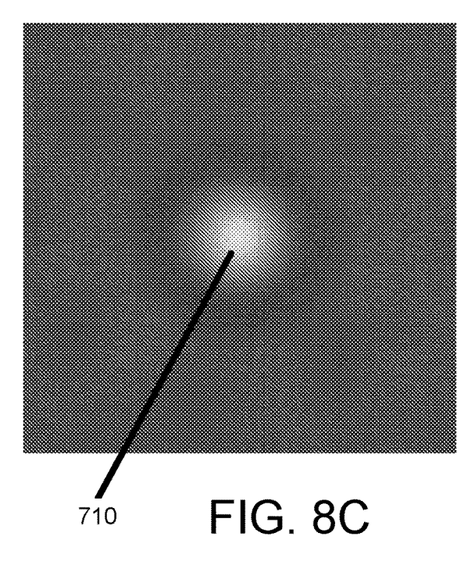

The results from the study are shown in FIGS. 8A-8C. As shown, FIG. 8A captured by the FPD displays a high-resolution image of the wire, that was approximately 2 mm away from the FPD. The full-width half-maximum (FWHM) of the reconstruction was approximately 1 pixel (about 83 µm). FIG. 8B shows the reconstructed image from the FPD of the target 702 within the phantom 704. The target was 15 cm above the FPD, and the FWHM of the image was approximately 247±4 µm. FIG. 8C is the image gathered by the CT detector when the target is placed alone on the CT bed without either the phantom or the FPD. It has a FWHM of approximately 720 µm.

Figure 9A:
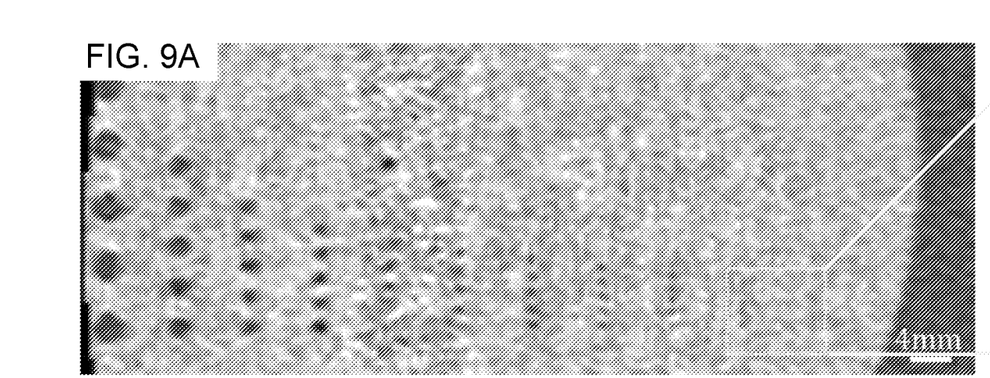
FIG. 9A is an image of a resolution target that includes holes of a range of sizes and spacings from the CT scanner alone at a radiation dose of CTDIvol=0.1 mGy and the hybrid system, at the same radiation dose of CTDIvol=0.1 mGy.
}
Figure 9B:
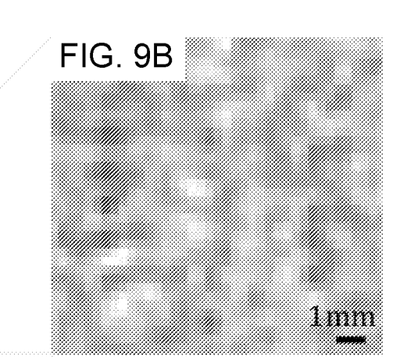
FIG. 9B is a magnified view of the smallest two sets of holes in the resolution target of FIG. 9A. The target includes holes of a range of sizes and spacings.
Figure 9C:
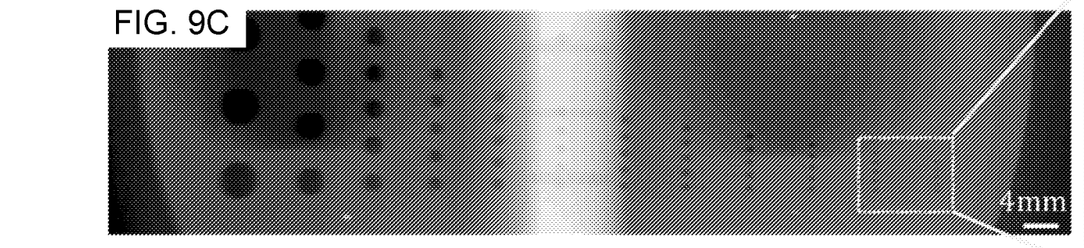
FIG. 9C is an image of a resolution target that includes holes of a range of sizes and spacings from the hybrid CT system.
Figure 9D:
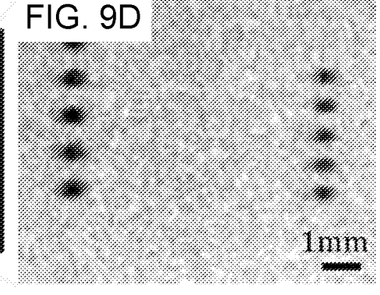
FIG. 9D is a magnified view of the image in FIG. 9C which shows that the smallest holes are clearly resolved.

FIGS. 9A-9D are a comparison of image resolutions of the hybrid system and the CT scanner alone, using the same very low radiation dose with the following parameters: CTDIvol=0.1 mGy, x-ray tube radiation output of 5 mAs. As seen in FIGS. 9C and 9D, the results show substantial improvement of resolution by the hybrid system. A resolution target with a series of holes in a range of sizes and spacings was scanned in the CT scanner alone at a radiation dose of CTDIvol=0.1 mGy to generate the image in FIG. 9A. The resulting image was then magnified 4×, as seen in FIG. 9B. In this magnified view, the smallest holes at the density of 12.5 line-pairs/cm cannot be resolved. The same resolution target was imaged with the hybrid CT system at the same radiation dose to generate the image in FIG. 9C. This image was then magnified 4×, as seen in FIG. 9D. In this magnified view, the smallest holes of 12.5 line-pairs/cm are clearly resolved.

It should be understood from the aforementioned descriptions that while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method for performing hybrid CT imaging using a whole body CT scanner, the method comprising:
   performing a full rotation CT scan;
   positioning one or more panel detectors in proximal to a patient in the whole body scanner;
   performing a hybrid CT scan, where the one or more panel detectors and a CT detector of the whole body CT scanner acquire data in parallel;
   performing a hybrid CT scan, where an x-ray source fires over the full rotation but with a time-varying intensity profile, such that an x-ray source intensity is greater over an arc opposite the one or more panel detectors, and lower in the rest of the rotation; and
   reconstructing a low-resolution and a high-resolution image from the acquired data.

2. The method of claim 1, where the data acquired by the CT detector during the hybrid scan is used to identify boundary conditions for the reconstruction of images from the panel detectors.

3. The method of claim 1, where the data acquired by the CT detector during the hybrid scan is used to identify the positions and orientations of the panel detectors.

4. The method of claim 1, where the data acquired by the CT detector during the hybrid scan is used to suppress low-spatial-frequency artifacts in the reconstruction of the high-resolution image.

5. The method of claim 1, where the data acquired by the CT detector during the hybrid scan is used for geometric calibration in situ.

6. The method of claim 1, where an x-ray source used during the hybrid scan is segmented to provide a plurality of x-ray beams.

7. The method of claim 6, where two or more regions of interest are simultaneously imaged during the hybrid scan.

8. The method of claim 1, where at least one flat panel detector of the one or more flat panel detectors is transparent to high-energy x-ray photons and wherein the at least one flat panel detector is positioned proximal to the region of interest during the full rotation CT scan.

9. The method of claim 1, where the data acquired by the CT detector are combined with the data acquired by the one or more panel detectors to reconstruct the high-resolution image.

\* \* \* \* \*